(12) United States Patent
Roa-Espinosa et al.

(10) Patent No.: US 10,919,828 B1
(45) Date of Patent: Feb. 16, 2021

(54) PROCESS FOR MANUFACTURING CANNABIDIOL

(71) Applicants: Aicardo Roa-Espinosa, Madison, WI (US); Joaquin Camilo Perez-Mahecha, Madison, WI (US); Michelle H Pham, Belleville, WI (US); Charles Kevin Jepson, Sioux Falls, SD (US)

(72) Inventors: Aicardo Roa-Espinosa, Madison, WI (US); Joaquin Camilo Perez-Mahecha, Madison, WI (US); Michelle H Pham, Belleville, WI (US); Charles Kevin Jepson, Sioux Falls, SD (US)

( * ) Notice: Subject to any disclaimer, the term of this patent is extended or adjusted under 35 U.S.C. 154(b) by 36 days.

(21) Appl. No.: 16/792,044

(22) Filed: Feb. 14, 2020

(51) Int. Cl.
*C07C 37/00* (2006.01)
*A23K 10/30* (2016.01)
*B01D 11/02* (2006.01)
*A23K 20/111* (2016.01)
*A23K 40/10* (2016.01)

(52) U.S. Cl.
CPC ............ *C07C 37/004* (2013.01); *A23K 10/30* (2016.05); *A23K 20/111* (2016.05); *A23K 40/10* (2016.05); *B01D 11/0288* (2013.01); *B01D 11/0296* (2013.01)

(58) Field of Classification Search
CPC ...... C07C 37/004; A23K 40/10; A23K 10/30; A23K 20/111
See application file for complete search history.

(56) References Cited

U.S. PATENT DOCUMENTS

| | | | | |
|---|---|---|---|---|
| 2,304,669 | A * | 12/1942 | Adams | C07C 37/004 568/743 |
| 8,895,078 | B2 * | 11/2014 | Mueller | A61K 31/35 424/725 |
| 9,950,275 | B1 * | 4/2018 | Ruben | C11B 3/006 |
| 10,308,625 | B1 * | 6/2019 | Ruben | C07C 37/70 |
| 10,532,942 | B1 * | 1/2020 | Roa-Espinosa | C02F 11/008 |
| 2012/0095087 | A1 * | 4/2012 | Hyatt | A61K 31/05 514/454 |
| 2017/0280740 | A1 * | 10/2017 | Goldstein | A61K 31/352 |
| 2018/0000857 | A1 * | 1/2018 | Kotra | A61K 31/775 |
| 2018/0206518 | A1 * | 7/2018 | Silver | |
| 2019/0015383 | A1 * | 1/2019 | Woelfel | A61K 31/05 |
| 2019/0117617 | A1 * | 4/2019 | Kariman | A61K 36/185 |
| 2019/0201463 | A1 * | 7/2019 | Kariman | A61K 36/185 |
| 2019/0210946 | A1 * | 7/2019 | Qu | B01D 15/1864 |
| 2019/0231833 | A1 * | 8/2019 | Garti | A61K 9/7023 |
| 2019/0241536 | A1 * | 8/2019 | Durkacz | C07C 37/004 |
| 2020/0039908 | A1 * | 2/2020 | ElSohly | A61K 31/05 |
| 2020/0155995 | A1 * | 5/2020 | Kolesinski | B01D 11/0288 |
| 2020/0222829 | A1 * | 7/2020 | Gildrien | B01D 3/14 |
| 2020/0261824 | A1 * | 8/2020 | Pal | B01D 37/00 |

FOREIGN PATENT DOCUMENTS

CN 103146564 A * 6/2013
WO WO-2019211795 A1 * 11/2019 ......... B01D 11/0211

OTHER PUBLICATIONS

B, Oomah et al., 76 Food Chemistry, 33-43 (2002) (Year: 2002).*
English-Language Machine Translation of CN 103146564 (2013) (Year: 2013).*

* cited by examiner

*Primary Examiner* — Alexander R Pagano
(74) *Attorney, Agent, or Firm* — Steven Greenfield; Greenfield Invention and Patent Consulting Inc.

(57) ABSTRACT

A process for producing cannabidiol from hemp and cannabis plants is disclosed. The steps of the process include the steps of: plant conditioning and size reduction, infusing with an extraction agent, separating a solid biomass and a liquid phase, treating the liquid phase with a removal agent, decarboxylation, removal of impurities; and color removal. The resulting cannabidiol conversion efficiency is over 90% and a TCH content within the legal limits for commercial cannabidiol.

15 Claims, 7 Drawing Sheets

PROCESS FOR MANUFACTURING CANNABIDIOL

FIELD OF THE INVENTION

The present invention relates generally to the field of manufacturing cannabidiol, also referred to as CBD oil. Cannabidiol has become the hot new product in states that have legalized medical marijuana. The non-intoxicating marijuana extract is being credited with helping treat a host of medical problems, e.g., epileptic seizures, anxiety, inflammation and sleeplessness.

BACKGROUND OF THE INVENTION

Cannabidiol, or CBD oil, is generally manufactured from the hemp and cannabis plants. The current processes used for manufacturing cannabidiol require expensive steps involving removal of undesirable materials at high temperature and pressure as well as a filtration step that requires a high purity alcohol that needs to be distilled for reuse; a step that presents a flammability hazard. The process of the present invention does not rely on any of these hazardous, complex and expensive steps and is less expensive and safer to carry out.

SUMMARY OF THE PRESENT INVENTION

In an aspect of the present invention, a process for producing cannabidiol comprises:
A. Providing biomass raw material feed;
B. Reducing the size of the biomass raw material feed to generate a macerated biomass stream;
C. Infusing the macerated biomass stream with an extraction agent to generate a treated biomass stream;
D. Separating the treated biomass stream into a stream containing primarily biomass solids and a predominantly liquid phase stream;
E. Converting a cannabidiolic acid component in the predominantly liquid phase stream into cannabidiol to generate a decarboxylated liquid phase stream; and
F. Removing impurities from the decarboxylated liquid phase stream to generate a clarified cannabidiol stream.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention.

Cannabis and hemp contain cannabidiolic acid, a.k.a. CBDA and tetrahydrocannabinol, a.k.a. THC as well as fibrous solids, color and aromatic materials. THC comes in several forms and is generally viewed as a material that could cause a variety of potentially undesirable health effects. CBDA is not known to produce such effects and is recognized as having beneficial health benefits only after it is converted to cannabidiol, a.k.a. CBD.

The raw material source for the production of cannabidiol includes the hemp and cannabis plants. Cannabis, or marijuana, and hemp contain THC that is the active ingredient in marijuana; however, hemp contains THC levels in the range of about 0.5% whereas cannabis contains levels as high as 12% and some high potency species of cannabis may contain even higher THC levels. Thus, a major challenge in producing Cannabidiol is reducing the level of THC in the CBD oil to the legal limit of about 0.3%. The higher the level of hemp in the initial mix of hemp and cannabis, the easier is to ensure that the legal limit of THC in CBD is not exceeded. Hemp and cannabis also comprise impurities including fatty materials, chlorophyll and various color materials. These impurities must also be removed to achieve the level of CBD purity required by consumers.

The current art for manufacturing CBD oil is to subject dried and ground cannabis biomass to the steps of 1) extraction, 2) winterization, 3) distillation and 4) isolation. For the extraction step, solvents such as supercritical $CO_2$, ethanol and or other hydrocarbons such pentane, hexane, and butane are used. Winterization is usually done to remove high melting point substances that may give the oil a turbid look or that can create issues in the distillation or isolation steps. This step is accomplished at very low temperatures that could be as low as −76 C depending on the extraction method used. A short path distillation step boils of the low boiling point solvents and the vapors are recovered in cooling coils for reuse. The final step is to isolate out the purified CBD oil.

This process requires complex and expensive steps and the risk of fire and explosions is ever present due to the use of hydrocarbon solvents. Thus, there is a need for a process that avoids these expensive steps and flammable solvents. Embodiments of the present invention process avoid the use of any flammable solvents and maybe accomplished at a significantly lower cost than the prior art processes while achieving CBD conversions from CBDA in the 95% to 98% range.

The process of the present invention is depicted in FIGS. 1-4. The process may include the following steps:
1) Conditioning of the cannabis and hemp plant biomass;
2) Cannabis plant biomass size reduction;
3) Mixing and infusing the reduced size biomass with an extracting agent that is selected from the group consisting of medium chain triglyceride (MCT) oils, ethanol and deionized water;
4) Separating the solid biomass from the liquid phase;
5) Treating the liquid phase with a removal agent;
6) Decarboxylation;
7) Removal of impurities; and
8) Color removal.

Figure 7:
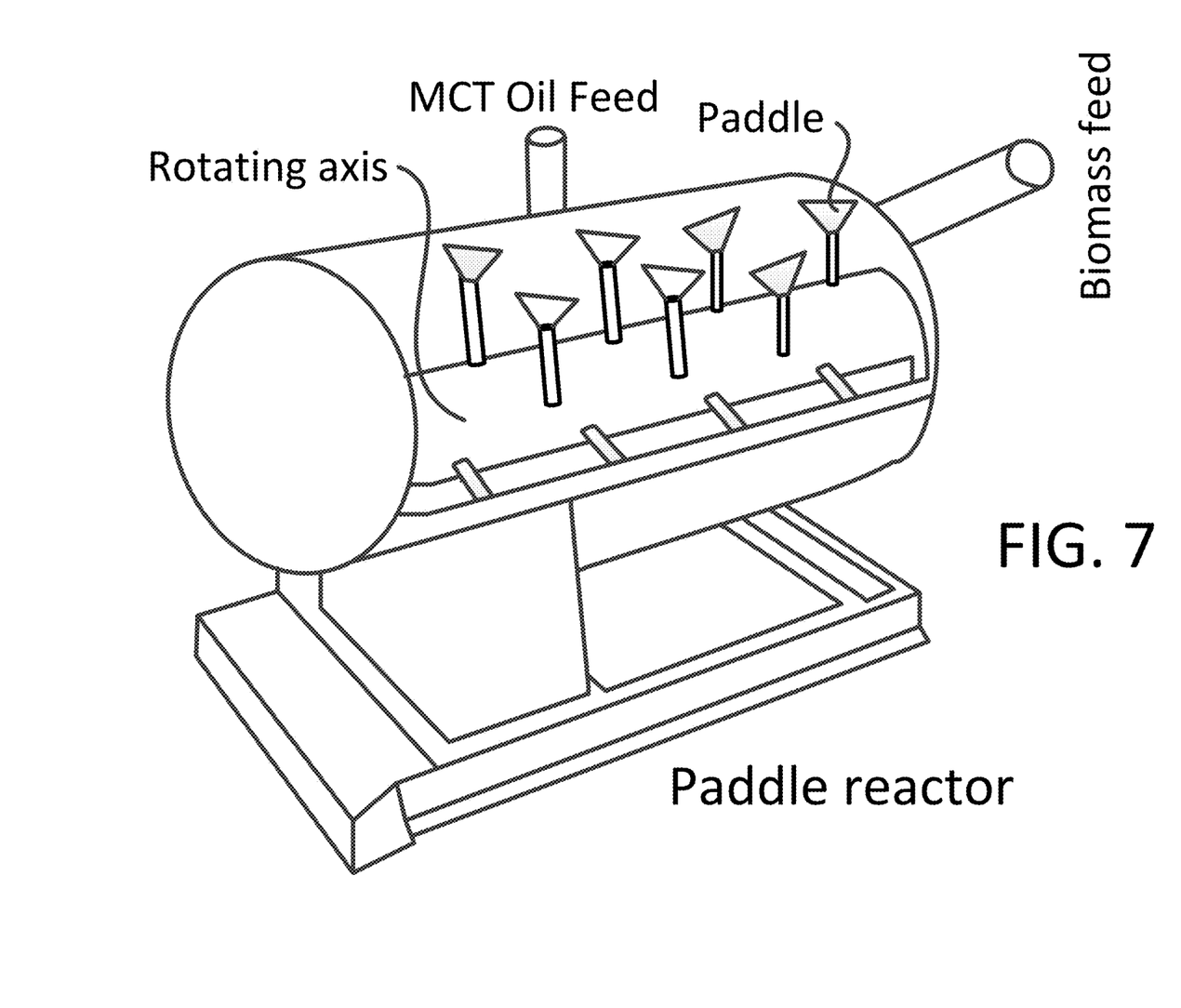
FIG. 7 portrays equipment used in the process for manufacturing cannabidiol from hemp and cannabis.

In the context of the present invention, hemp and cannabis biomass contain the leaves, stems and seeds of the plant dried to a range of 92% to 98% solids. The conditioning and size reduction are accomplished in a paddle reactor shown in FIG. 7. The paddles rotate around an axis at a high speed and macerate the cannabis biomass into particulate form as they are introduced into the paddle reactor by imparting high shear forces to the biomass.

Conditioning the biomass facilitates the release of the CBDA oil from the biomass. This may include: 1) drying the biomass to a moisture of less than 15% and 2) treating the biomass using a conditioning agent.

The preferred conditioning agents are selected from the following compositions: a) sodium or potassium anionic acrylate acrylamide copolymer having about 5% to 90% charge and a weight average molecular weight of 6 million to about 18 million, b) acrylamide/Ethanaminium N,N,N-trimethyl-2-((1-oxo-2-propenyl)oxo)-, chloride copolymer, c) cationic tannin, d) the chloride salt form of the rare earth metals having atomic numbers from 57 through 71, e) zinc chloride and combinations of the above. The preferred rare earth element is lanthanum. Conditioning agent treatment levels may range from about 1 to 50 mg/kg of biomass. In an embodiment of the present invention process, the pH of the paddle mixer contents is adjusted to about 2 to 3. The adjustment of pH may be accomplished with any acid; however, the preferred acid is phosphoric acid.

The contents of the paddle reactor may be heated to a temperature of between 60 to about 90 degrees C. The desired particle size resulting from the maceration step in the paddle reactor is <4 mm. Particles larger than 4 mm may be screened out and hammer-milled to reduce the average particle size to <4 mm.

In the following step, an extraction agent is introduced into the paddle reactor at about a 1:1 ratio by weight and mixed with the dried biomass; however, the ratio may range from about 0.5:1 to 1.5:1. One extraction agent is an MCT oil, preferably refined coconut oil and/or refined hemp oil; however; other MCT oils fall within the scope of the present process. The infusion results in the extraction and release of the CBDA content from the biomass and combination with the MCT oils. It is also noted that the steps of cannabis feed size reduction in the paddle reactor and the infusion with the MCT oils run concurrently. The process using MCT oils is described in FIGS. 1 and 2.

Other extraction agents that fall within the scope of the present invention include ethanol and deionized water. The process using deionized water as the extraction agent is described in FIG. 4 while the process using ethanol as the extraction agent is described in FIG. 3.

Figure 2:
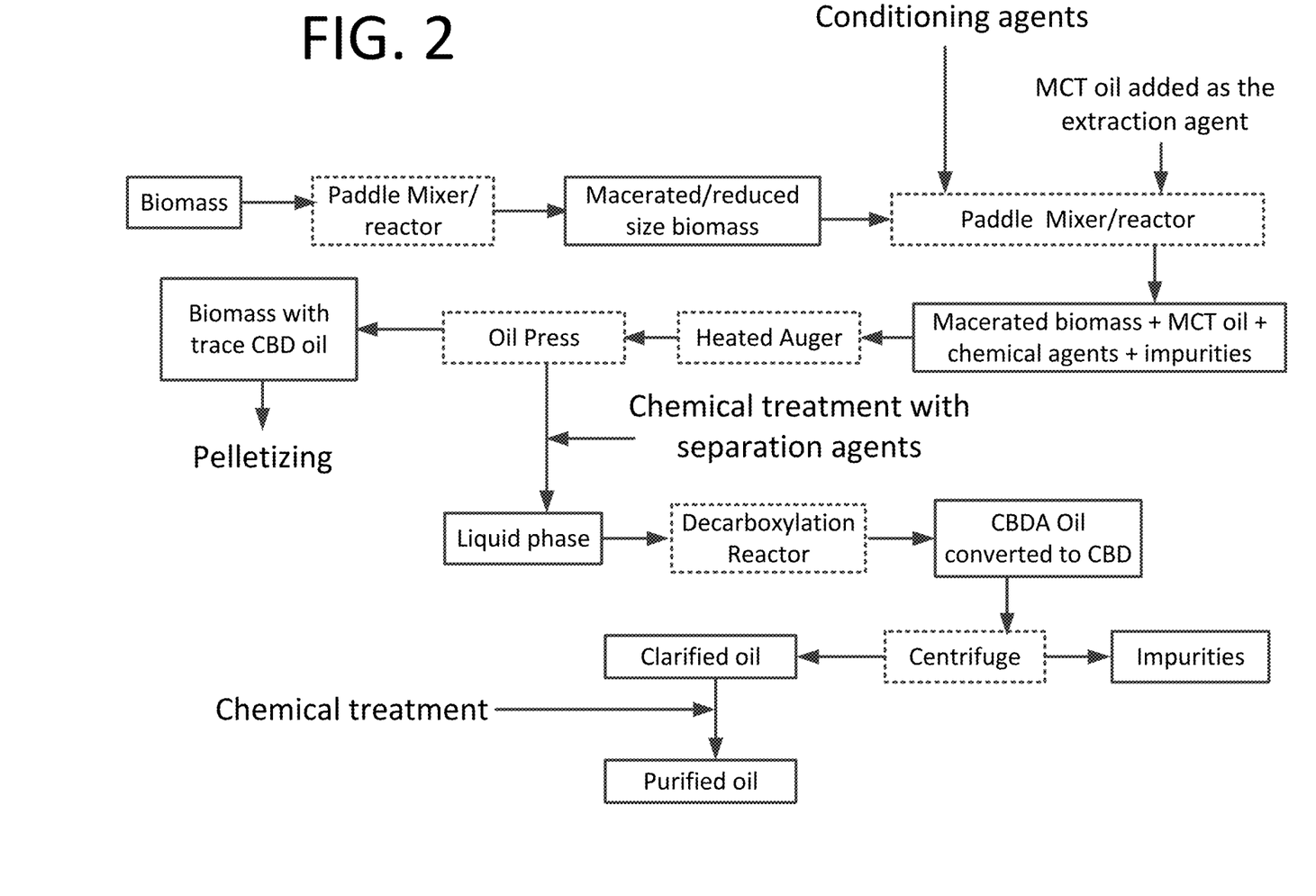
FIGS. 2-4 show schematics of process embodiments for manufacturing cannabidiol from hemp and cannabis.
Figure 3:
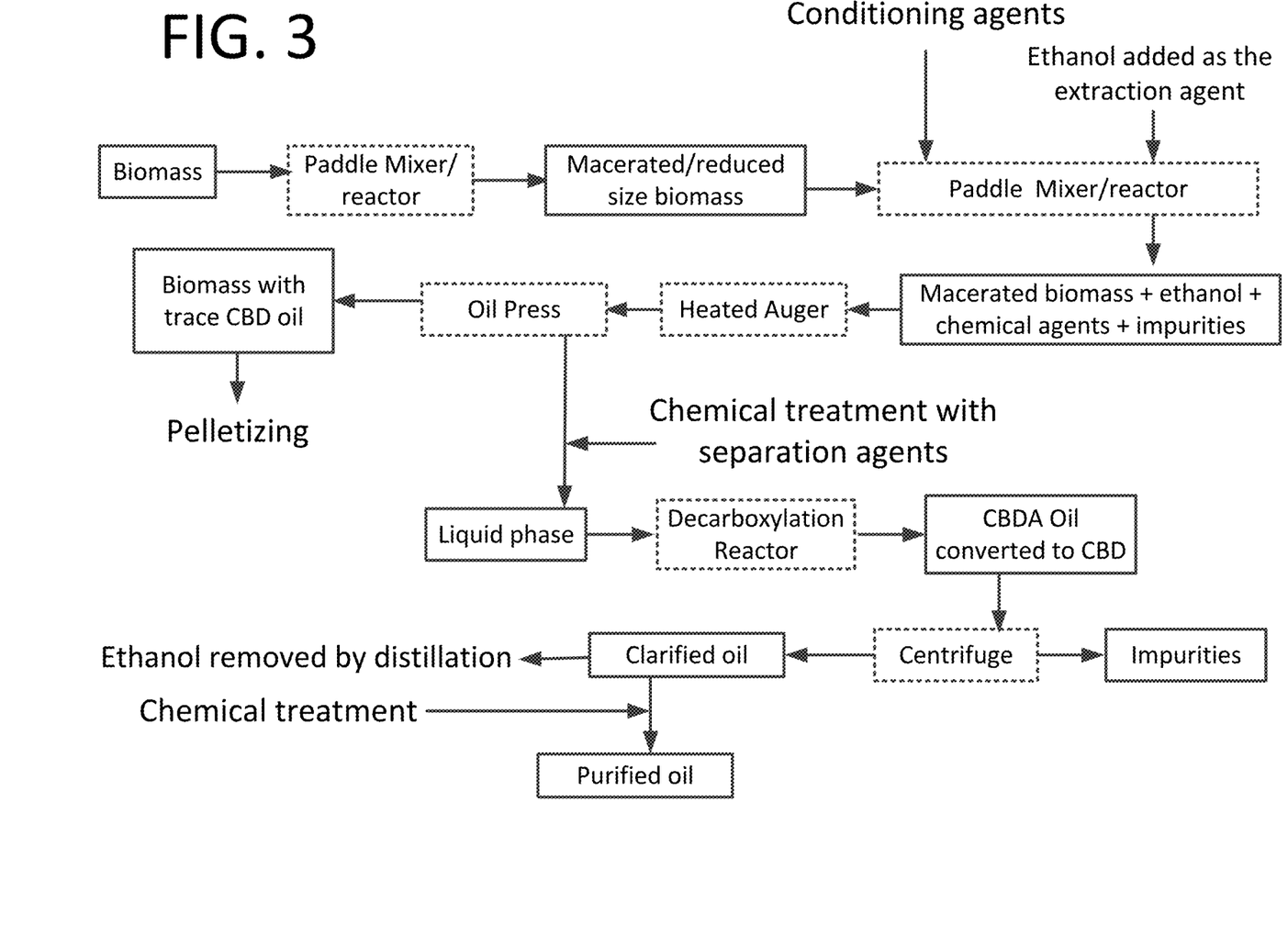
Figure 4:
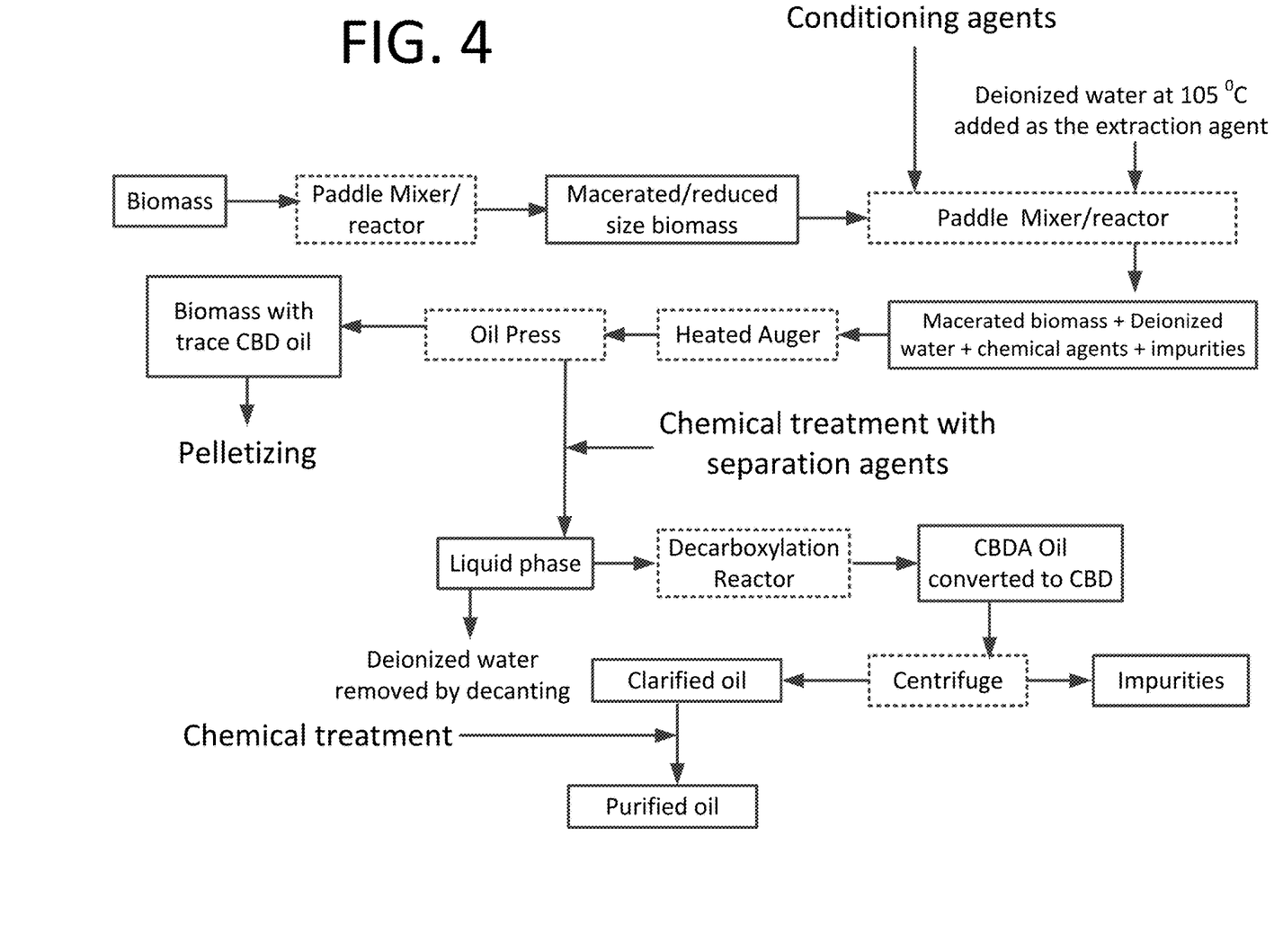

In the third step following the maceration, extraction and optionally conditioning steps carried out in the paddle reactor, the mixture containing the biomass, the conditioning agent and extraction agent is passed through an oil press at about 60-90 degrees C. The oil press separates the mixture to 1) a predominantly solid phase that contains biomass fibers with small amounts of oil and agents added to the paddle reactor and 2) a predominantly liquid phase that contains mostly oil with small amounts of fiber, treatment chemicals and impurities. Prior to the hot oil pressing, the mixture exiting the paddle reactor may be heated in an augur to the hot oil press temperature as shown in FIGS. 2-4.

Figure 6:
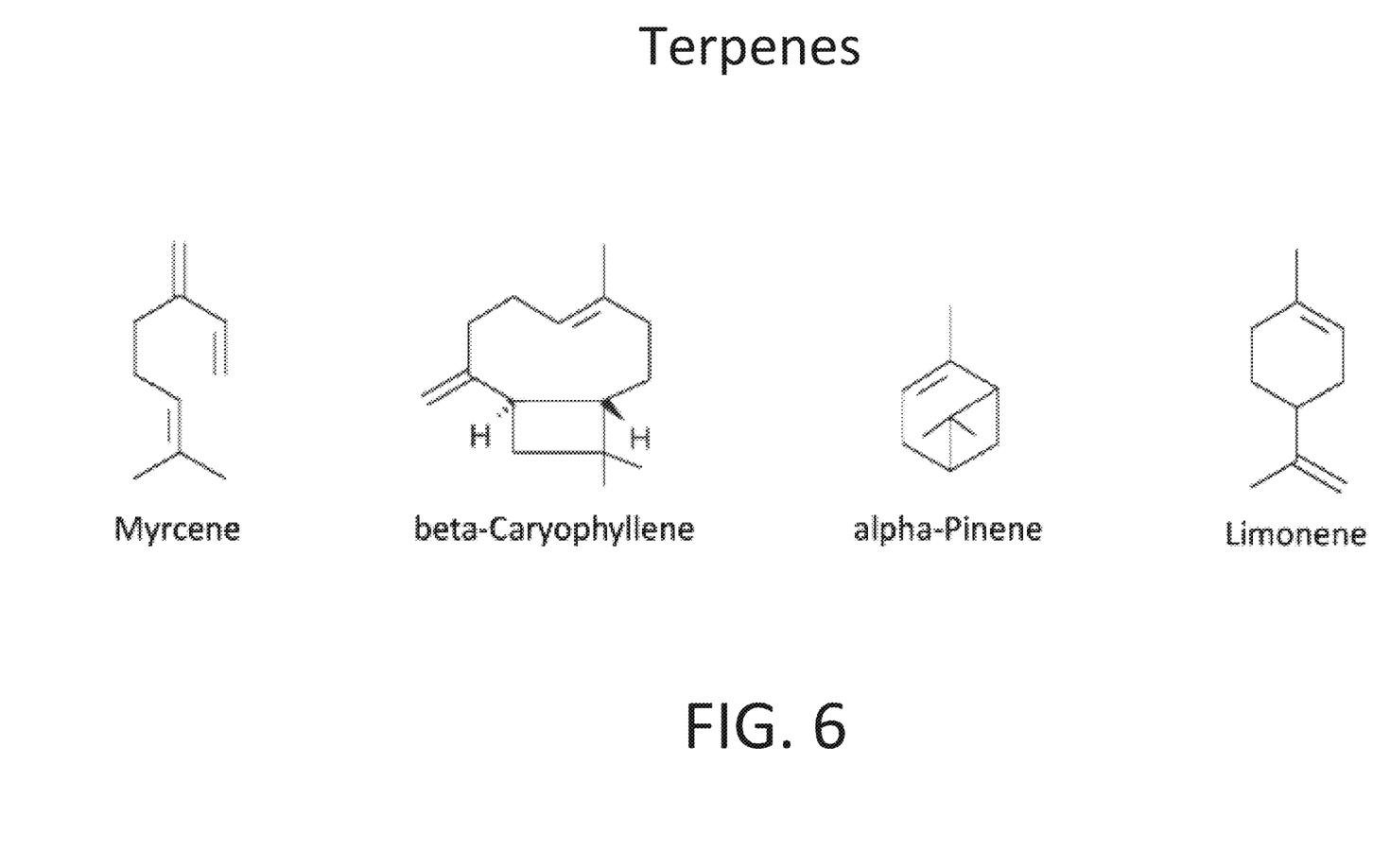
FIG. 6 shows the chemical structures of components in the present in the raw materials that take part in the process for manufacturing cannabidiol from hemp and cannabis.

The resulting liquid phase contains cannabidiolic acid, referred to as CBDA, small amounts of cannabidiol, referred to as CBD, impurities such as waxes, fatty acids and chlorophyll that imparts a dark color to the filtered oil. These impurities are undesirable and need to be removed in order to produce a commercial grade CBD oil product. Some of the impurities are terpenes that impart the oils with a distinct aroma and therefore are not considered undesirable impurities. The chemical structures of common terpenes present in the cannabis and hemp biomass are shown in FIG. 6. If the extracting agent is either ethanol or deionized water, they need to be removed from the final product; however, if the extracting agent is an MCT oil, its removal from the final product is not necessary.

Next, the liquid phase is treated with a separation catalyst that helps precipitate the impurities within 15-30 minutes. Suitable separation catalysts that fall in the scope of the present invention include a) sodium or potassium anionic acrylate acrylamide copolymer having 5% to about 90% charge and a weight average molecular weight of 6 million to about 18 million, b) cationic tannin c) acrylamide/Ethanaminium N,N,N-trimethyl-2-((1-oxo-2-propenyl) oxo)-, chloride copolymer, d) the chloride salt form of the rare earth metals having atomic numbers from 57 through 71, e) zinc chloride and combinations of the above. The preferred rare earth element is lanthanum. Separation catalyst treatment levels may range from 1-50 mg/liter of the liquid phase. The use of a separation catalyst is more beneficial when the extraction agent is either ethanol or deionized water but may also be used if the extraction agent is an MCT oil. It is noted that the agents that are used for extracting the CBDA oil from the biomass are also useable as conditioning agents added to the paddle reactor.

Figure 5:
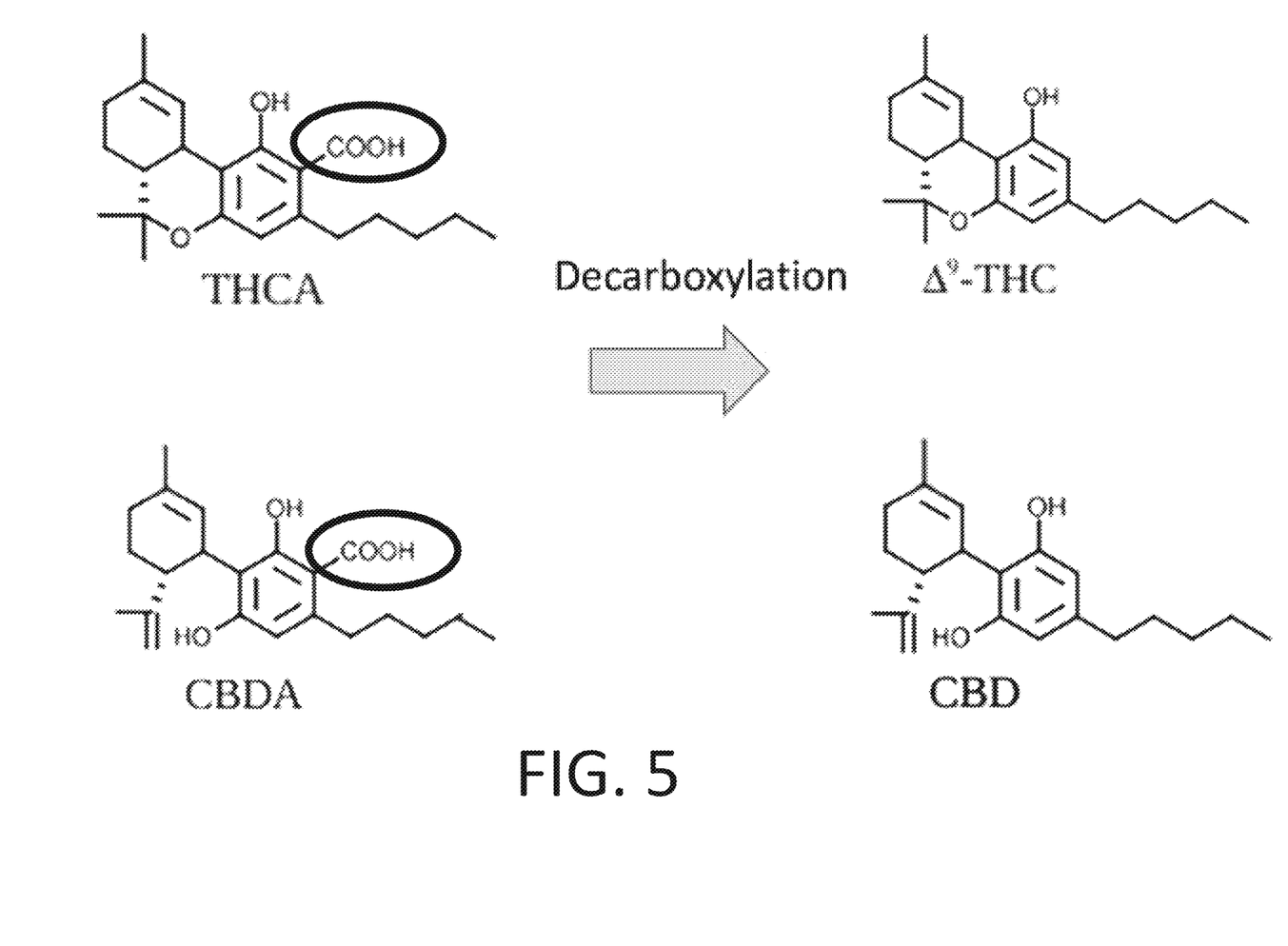
FIG. 5 illustrates the reactions that take place among the key components in the process for manufacturing cannabidiol from hemp and cannabis.

The next step depends on the extraction agent added to the paddle reactor. If and MCT oil is used, the treated liquid phase is heated to between 120 to about 150 degrees C. for about 60 minutes. This causes the CBDA to convert to CBD at conversion levels exceeding 98%. The resulting decarboxylated oil contains primarily CBD as well as small amounts of CBDA and impurities as shown in Table 1 in the Examples section. As shown in FIG. 5, decarboxylation results in the removal of the COOH which is the acid group in the CBDA and THCA resulting in the conversion of CBDA into CBD and THCA into a non-acid form of TCH referred to as $\Delta^9$ TCH. This process is described in FIG. 2.

Following decarboxylation, the impurities are removed from the decarboxylated filtered oil by centrifugation and allowing the impurities to settle out to the bottom of the liquid phase where they may be removed by gravity leaving a clarified oil phase in the treatment vessel. The clarified oil may be further treated with phosphoric acid having an activity strength of about 85% in an amount of about 2% to about 3% by dry weight of clarified filtered oil. The clarified oil may still have a tinge of dark color even after the impurities' removal step. The treatment with the phosphoric acid bleaches any dark color that might be showing after the centrifuging step.

One of the preferred medium chain triglyceride oils, i.e., refined coconut oil, used in the second step is available commercially. However, a second preferred medium chain triglyceride oil, i.e., refined hemp oil, is not available commercially and must be produced in a separate step. In an embodiment of the present invention, the hemp oil is produced using the following steps:

1. Pressing hemp seeds in a heated oil press at a temperature in a range of 60 to about 90 degrees C. This step presses out filtered hemp oil.

Figure 1:
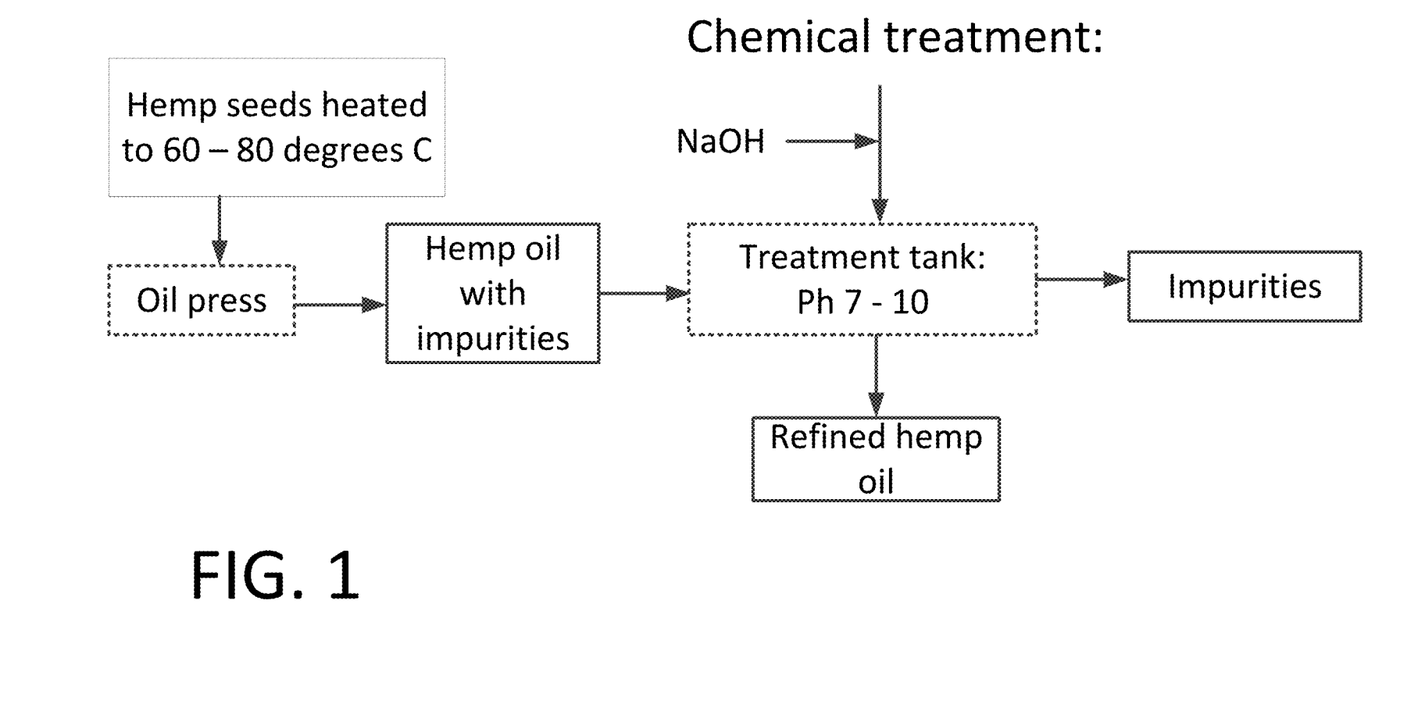
FIG. 1 presents a schematic of one step of a process for manufacturing cannabidiol from hemp and cannabis.

2. Treating the filtered hemp oil chemically to precipitate out the impurities. Materials that may be used for the treatment include cationic and anionic tannin as well as other coagulants and flocculants. The process for making refined hemp oil is shown in FIG. 1.

It is noted that in the context of this patent application, the term "filtered oil" refers to oil that contains impurities while the terms "clarified oil" and "refined oil" refer to oils from which the impurities have been removed.

If the extraction agent is ethanol, the step following the oil press is to remove the ethanol from the liquid phase. This is done by distillation using a standard distillation process in which the liquid phase is heated to the ethanol boiling point and the resulting ethanol vapors are re-condensed into liquid ethanol for reuse. The ethanol distillation step may be carried out either before or after the decarboxylation and the centrifuging steps.

If the extraction agent is deionized water, the liquid phase is allowed to settle causing the water and oil phases to separate. The heavier water phase settles to the bottom while the lighter oil phase floats to the top. The phases may be separated by either decanting the oil or removing the water by gravity from the bottom.

Below is information about the compositions and properties of the treatment chemicals added in the processes of the present invention:

Tannin

Weight average molecular weight between 10,000 and 300,000
Liquid form with 30 to 40% concentration
Cationic site on the main chain
Viscosity at 50% of between 40 and 2000 centipoises
Comes in various forms such as tannic acid $C_{17}H_{16}O_9$ and gallic acid $C_7H_6O_5$. May be made having an anionic charge or a cationic charge.

Sodium or Potassium Anionic Acrylate Acrylamide Copolymer

This polymer may be made from the reaction between an acrylamide monomer and an acrylic acid monomer as shown below.

Sodium Acrylate Acrylamide copolymer

Cationic Acrylamide Copolymer

ADMAEA
  Acrylamide-dimethylaminoethyl acrylate copolymers.
  The copolymerization of DMAEA-MeCl with acrylamide produces the cationic polymer.
  The main characteristics of the products obtained are:
    Weight average molecular weight: about 3 million to about 10 million.
    Viscosity at 5 g/l: 100 to 1700 cps.
    Specifically: acrylamide/Ethanaminium, N,N,N-trimethyl-2-((1-oxo-2-propenyl)oxo)-, chloride copolymer is a useful form of ADMAEA in the present invention. The molecular formula is $C_{11}H_{21}ClN_2O_3$. The molecular structure is shown below in 2D.

EXAMPLES

The table below presents test results in the feed materials and the materials produced in the various steps of the process. As can be seen, over 92% of the initial CBDA content of 4.7% is converted into CBD in the clarified oil. The final THC level is below the legal limit. It is noted that terpenes are not present in the final product having been removed with the impurities in the process.

| | Weight % | | | |
|---|---|---|---|---|
| Component | Dried Biomass | Filtered oil | Decarboxylated oil | Clarified oil |
| CBDA | 4.68 | 4.76 | 0.08 | 0.03 |
| CBD | 0.57 | 0.52 | 4.4 | 4.32 |
| THC | 0.49 | 0.36 | 0.42 | 0.17 |

We claim:
1. A process for producing cannabidiol comprising the steps of:
   A. Providing biomass raw material feed;
   B. Reducing the size of the biomass raw material feed to generate a macerated biomass stream;
   C. Infusing the macerated biomass stream with an extraction agent to generate a treated biomass stream, the extraction agent being selected from the group consisting of 1) an oil having a medium triglyceride chain, 2) ethanol and 3) deionized water, wherein steps B and C are carried out concurrently at a temperature of between 60 to about 90 degrees C. in a paddle reactor;

D. Separating the treated biomass stream into a stream containing primarily biomass solids and a predominantly liquid phase stream;

E. Converting a cannabidiolic acid component in the predominantly liquid phase stream into cannabidiol to generate a decarboxylated liquid phase stream; and F. Removing impurities from the decarboxylated liquid phase stream to generate a clarified cannabidiol stream.

2. The process of claim 1, wherein the oil having a medium triglyceride chain is selected from the group consisting of refined coconut oil and clarified hemp oil.

3. The process of claim 1, wherein the extraction agent is mixed with the biomass feed at a ratio of between 0.5 to about 1.5 by weight.

4. The process of claim 1, wherein separating the treated biomass stream into a stream containing predominantly biomass solids and a predominantly liquid phase stream is accomplished by passing the treated biomass stream in an oil press at a temperature of about 60-90 degrees C.

5. The process of claim 4, wherein converting the cannabidiolic acid component in the predominantly liquid phase stream into cannabidiol to generate a decarboxylated liquid phase stream is accomplished by heating the cannabidiolic acid component to a temperature of at least 120 degrees C. for about 60 minutes in a decarboxylation reactor.

6. The process of claim 4, further comprising treating the liquid phase stream with a separation catalyst selected from the group consisting of a) sodium or potassium anionic acrylate acrylamide copolymer having 5% to about 90% charge and a weight average molecular weight of 6 million to about 18 million, b) cationic tannin c) acrylamide/Ethanaminium N,N,N-trimethyl-2-((1-oxo-2-propenyl) oxo)-, chloride copolymer, d) the chloride salt form of the rare earth metals having atomic numbers from 57 through 71, e) zinc chloride and f) combinations of the above, the separation catalyst being added at an amount of about 1 to about 50 mg/liter of the liquid phase.

7. The process of claim 5, wherein removing impurities from the decarboxylated liquid phase stream to generate a clarified cannabidiol stream comprises centrifuging the decarboxylated liquid phase stream and separating out a settled impurities layer from the clarified cannabidiol stream by gravity.

8. The process of claim 4, further comprising removing the ethanol from the liquid phase stream by distillation and recovering a distilled ethanol stream for reuse in the process.

9. The process of claim 4, further comprising removing the deionized water from the liquid phase stream by gravity.

10. The process of claim 7, further comprising treating the clarified cannabidiol stream with phosphoric acid at an amount of 2.0% to about 3.0% by weight of the clarified cannabidiol stream.

11. The process of claim 4, further comprising converting the stream containing primarily biomass solids into pellets for use as animal feed.

12. The process of claim 1, wherein the biomass raw material feed comprises cannabis and hemp.

13. The process of claim 1, wherein the size of the biomass raw material feed is reduced to less than 4 mm in the paddle reactor.

14. The process of claim 1, wherein steps B and C are carried out at a pH of about 2 to 3, wherein said pH is adjusted using an acid.

15. The process of claim 14, wherein the acid is phosphoric acid.

* * * * *